United States Patent [19]

Murugan et al.

[11] Patent Number: 5,508,410
[45] Date of Patent: Apr. 16, 1996

[54] PROCESS FOR PREPARING 2-HALO-5-SUBSTITUTED PYRIDINES

[75] Inventors: Ramiah Murugan, Indianapolis; Eric F. V. Scriven, Greenwood; Tony Y. Zhang, Indianapolis, all of Ind.

[73] Assignee: Reilly Industries, Inc., Indianapolis, Ind.

[21] Appl. No.: 160,037

[22] Filed: Nov. 30, 1993

[51] Int. Cl.$^6$ .................................................. C07D 213/61
[52] U.S. Cl. ............................................ 546/250; 546/253
[58] Field of Search ................................... 546/250, 253

[56] References Cited

U.S. PATENT DOCUMENTS

| | | | |
|---|---|---|---|
| 4,504,664 | 3/1985 | Nelson et al. | 546/243 |
| 4,584,380 | 4/1986 | Hartmann | 546/250 |
| 4,599,422 | 7/1986 | Amey | 546/251 |
| 4,778,896 | 10/1988 | Gallenkamp | 546/304 |
| 5,053,516 | 10/1991 | Hartmann et al. | 546/251 |
| 5,099,025 | 3/1992 | Kaufmann et al. | 546/345 |
| 5,198,549 | 3/1993 | Gunther | 546/345 |
| 5,229,519 | 7/1993 | Zhang | 546/250 |

FOREIGN PATENT DOCUMENTS

| | | |
|---|---|---|
| 0108483 | 9/1983 | European Pat. Off. . |
| 0121320 | 7/1984 | European Pat. Off. . |
| 0546418A1 | 11/1992 | European Pat. Off. . |
| 4111214A1 | 8/1992 | Germany . |

OTHER PUBLICATIONS

Meth–Cohn et al., "A Versatile New Synthesis of Quinolines and Related Fused Pyridines Part 12, A General Synthesis of 2–Chloropyridines and 2–Pyridones", *J. Chem. Soc.* Perkin Trans. 1 pp. 1173–1182 (1984).

Barton et al., "Convenient Synthesis of 5–Substituted 2–Hydroxybenzoates and Related Reactions", *J. Chem. Soc.* Perkin 1 pp. 665–669 (1982).

Aadil et al., "Synthesis of 4.5 Disubstituted 2–Chloronicotinates", *Synthetic Comm.*, vol. 23, No. 18, pp. 2587–2592 (1993).

Marson, "Tetrahedron Report No. 312, Reactions of Carbonyl Compounds with (Monohalo) Methyleniminium Salts (Vilsmeier Reagents)", *Tetrahedron*, vol. 48, No. 18, pp. 3659–3726 (1992).

Chemical Abstracts 119:27973, 1993, abstract of Zhang, Zhenquan, "Isomerization of gamma–formyul nitriles to pyridones catalyzed by Organotin", *Huaxue Xuebao*, 51(2), pp. 191–196.

*Primary Examiner*—C. Warren Ivy
*Assistant Examiner*—D. Margaret M. Mach
*Attorney, Agent, or Firm*—Woodard, Emhardt, Naughton, Moriarty & McNett

[57] ABSTRACT

Described are preferred processes for preparing 2-halo-5-substituted pyridine compounds. Preferred processes can be conducted in a one-step, one-pot fashion, and involve the reaction of a formamide and a halogenating agent with a nitrile such as cis-2-pentenonitrile or with a combination of reactants including an aldehyde such as n-propionaldehyde and a nitrile or an amide. Preferred processes provide for convenient and advantageous preparations of 2-chloro-5-methylpyridine, which serves as an intermediate to important insecticidal compounds.

26 Claims, No Drawings

PROCESS FOR PREPARING 2-HALO-5-SUBSTITUTED PYRIDINES

BACKGROUND

The present invention relates generally to pyridine compounds, and more particularly to a unique process for preparing 2-chloro-5-substituted pyridine compounds.

As further background, substituted pyridine compounds such as 2-halo-5-substituted pyridines are useful inter alia as insecticides or herbicides, or as intermediates for preparing insecticides, herbicides and pharmaceuticals. For example, one such compound, 2-chloro-5-methylpyridine, finds use as an intermediate to imidacloprid, a compound receiving substantial attention as an insecticide.

As to their preparation, 2-halo-5-substituted pyridines can be prepared by halogenation of a corresponding 5-substituted pyridine. However, such halogenations are difficult to control and generally not selective, leading to mono- and dichlorination on alkyl substituents at the 5 position and substantial dichlorination of the pyridine ring at the 1 and 6 positions.

2-Halo-5-substituted pyridines can also be prepared from their corresponding 2-amino-5-substituted pyridines as, for example, described in German Patent No. 4111214 to Bayer A. G. However, this route requires the formation of the aminopyridine and would be relatively disadvantageous compared to an effective process directly providing the desired 2-halo-5-substituted pyridine.

U.S. Pat. No. 5,099,025 describes the preparation of 2-chloro-5-methylpyridine, which involves reacting the N-oxide of 3-methylpyridine with certain sulphonyl or sulphanoyl chlorides in the presence of a basic organic nitrogen compound and a diluent at a temperature between about −120° C. and 150° C. However, such processes require the formation of the N-oxide and are also of a relatively complex nature.

Additional background information to the present invention may be found in U.S. Pat. Nos. 5,053,516; 4,504,664; 5,229,159; and in European Patent Applications 108483 (1984); 121320 (1984) and 546418 (1993).

In light of the background in the area, there remains a need for a relatively simple process for preparing 2-halo-5-substituted pyridine compounds such as 2-chloro-5-methylpyridine. Preferred processes would minimize the number of steps required to achieve the desired product and utilize readily available and inexpensive starting materials. The applicant's invention addresses these needs.

SUMMARY OF THE INVENTION

Accordingly, in one preferred embodiment of the present invention provides a process for preparing a 2-halo-5-substituted pyridine compound which includes reacting a dialkylformamide or an arylalkylformamide, in the presence of a halogenating agent, with an amide or nitrile of the formula:

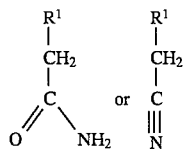

wherein $R^1$ is —H or an alkyl, haloalkyl, alkenyl, aryl, arylalkyl, ester or halogen group, and an aldehyde of the formula:

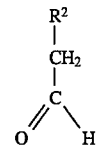

wherein $R^2$ is an alkyl, haloalkyl, alkenyl, aryl, arylalkyl, ester or halogen group, so as to form the 2-halo-5-substituted pyridine compound.

Another preferred embodiment of the invention provides a process for preparing a 2-halo-5-substituted pyridine compound, which includes reacting a dialkylformamide or an arylalkylformamide, in the presence of a halogenating agent, with a compound of the formula:

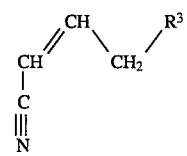

wherein $R^3$ is an alkyl, haloalkyl, alkenyl, aryl, arylalkyl or halogen group, so as to form a 2-halo-5-substituted pyridine compound.

Still another preferred embodiment of the present invention provides a process for preparing 2-chloro-5-methylpyridine, which includes reacting dimethylformamide, in the presence of a chlorinating agent, with (i) acetonitrile or acetamide and n-propionaldehyde or (ii) cis-2-pentenonitrile, so as to form 2-chloro-5-methylpyridine.

The invention provides processes for preparing 2-halo-5-substituted pyridine compounds such as 2-chloro-5-methylpyridine, which are useful as or as intermediates to insecticides, pharmaceuticals or herbicides. Preferred processes of the invention utilize readily available and inexpensive starting materials, and can be conducted in a one-step, one-pot fashion at convenient temperatures and pressures.

Additional preferred features, objects and advantages of the invention will be apparent from the description which follows.

DESCRIPTION OF THE PREFERRED EMBODIMENT

For the purposes of promoting an understanding of the principles of the invention, reference will now be made to certain embodiments thereof and specific language will be used to describe the same. It will nevertheless be understood that no limitation of the scope of the invention is thereby intended, such alterations, further modifications, and applications of the principles of the invention as illustrated herein being contemplated as would normally occur to one skilled in the art to which the invention relates.

As indicated above, the invention provides processes for preparing 2-halo-5-substituted pyridine compounds and in one especially preferred aspect provides processes for preparing 2-chloro-5-methylpyridine. Such compounds are useful, among other things, as or as intermediates to pharmaceuticals, insecticides and herbicides.

The starting materials used in the present invention will include an appropriate formamide, e.g. a dialkylformamide or arylalkylformamide. As examples, suitable dialkylformamides will include those where the alkyl groups are about $C_1$ to $C_{10}$ alkyl groups, which alkyl groups may be the same as or differ from each other. Suitable dialkylformamides will thus include materials such as dimethylformamide, diethylformamide, dipropylformamide, etc. As well, the dialkylformamides used in the invention can be cyclic dialkylformamides such as N-formylpiperidine. Arylalkylformamides which can be used in the present invention include, for instance, N-phenyl-N-methylformamide. Given the disclosure herein, those skilled in the art will be readily able to select and utilize suitable formamides in the inventive process.

Processes of the invention will also be conducted in the presence of a halogenating agent, e.g. a chlorinating or brominating agent. Among these, chlorinating agents are preferred so as to provide 2-chloropyridine derivatives. Suitable halogenating agents will be readily selected and used by the skilled artisan in the invention, and include materials such as phosphorus oxychloride, phosphorus pentachloride, phosgene, oxaloyl chloride, thionyl chloride, phosphorus oxybromide, phosphorus tribromide, and the like.

In accordance with the invention, the halogenating agent and the formamide will be reacted with another material or materials so as to form a 2-halo-5-substituted pyridine compound. In one preferred aspect, the formamide and halogenating agent are reacted with an amide or nitrile of the formula:

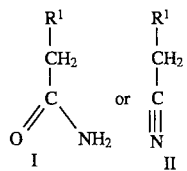

wherein $R^1$ is a group which is not transformed under the conditions of the reacting, preferably a group such as an alkyl, haloalkyl, alkenyl, aryl, arylalkyl, ester or halogen group, in combination with an aldehyde of the formula:

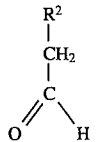

wherein $R^2$ is likewise a group which is not transformed under the conditions of the reacting, such as an alkyl, haloalkyl, alkenyl, aryl, arylalkyl, ester or halogen group. These materials react in one-step, one-pot fashion to provide a 2-halo-5-substituted pyridine compound.

In another preferred aspect of the invention, the formamide and halogenating agent are reacted with a nitrile compound of the formula:

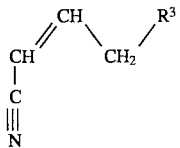

wherein $R^3$ is a group that is not transformed under the conditions of the reacting, for example an alkyl, haloalkyl, alkenyl, aryl, arylalkyl or halogen group. This nitrile compound, in the presence of the halogenating agent and formamide, reacts to form the 2-halo-5-substituted pyridine compound. In accordance with this aspect of the invention, the reacting can be in the presence of other materials which may be converted to the desired 2-halo-5-substituted pyridine compound, for example, the combined aldehyde (Formula III) and nitrile (Formula I) or amide (Formula II) reactants identified above. Likewise, in the above aspect, the reaction of the aldehyde (III) and nitrile (I) or amide (II) could be in the presence of a nitrile of the Formula IV which also forms the 2-halo-5-substituted pyridine compound.

As has been indicated above, reactants of the invention can contain an alkyl, haloalkyl, alkenyl, aryl, arylalkyl or halogen group. In these groups, alkyl and alkenyl groups are preferably about $C_1$ to about $C_{10}$ (i.e. contain 1 to about 10 carbons). Aryl groups are preferably about $C_6$ to about $C_{30}$, especially phenyl or naphthyl, and arylalkyl groups are preferably groups of the formula $-(CH_2)_n$-aryl wherein n is an integer from about 1 to 3. Halo or halogen groups are preferably chloro or bromo, and thus haloalkyls can include mono- or poly-chlorinated or mono- or poly-brominated alkyl groups such as chloromethyl or bromomethyl, mono- or poly-chlorinated ethyl, propyl, butyl, pentyl, etc. groups. Ester groups will have the formula $-COO-R^4$ wherein $R^4$ can be an alkyl, haloalkyl, aryl, or arylalkyl group.

As to conditions of reacting, reactions of the invention can be conducted in a wide temperature range, for example, from about $-10°$ to about $150°$ C., more preferably from ambient temperatures (e.g. about $20°$ C.) up to about $100°$ C. Similarly, inventive reactions can be conducted in a wide range of solvents, including the use of reactants such as the halogenating agent (e.g. phosphorus oxychloride) or formamide (e.g. dimethylformamide) in excess as the solvent, or other inert solvents such as chlorinated lower alkyls (i.e. $C_1$ to $C_5$ alkyls), e.g. dichloromethane, chloroform, 1,2-dichloroethane, and the like. Processes of the invention are preferably but not necessarily conducted under anhydrous conditions. When water is present there will of course be the need to use additional amounts of phosphorus oxychloride or other halogenating agents which are depleted in the presence of water. Processes of the invention can also be conducted at a wide range of pressures, including subatmospheric, ambient and superatmospheric pressures. These and similar details of reactions of the invention will be readily determined by those skilled in the art.

2-Halo-5-substituted pyridine compounds produced in accordance with the invention can be conventionally recovered, for example utilizing techniques such as extraction, evaporation of the solvent, and other similar techniques. Similarly, products of the invention can be conventionally employed as or as intermediates to pharmaceuticals, insecticides, or herbicides.

In order to promote a further understanding of tile present invention and its features and advantages, the following specific Examples are provided. It will be understood that these Examples are illustrative and not limiting in nature.

EXAMPLE 1

Preparation of 2-chloro-5-methylpyridine

To a mixture of acetonitrile (0.1 mole) and N-propionaldehyde (0.1 mole) in dimethylformamide (50 mL) was added phosphorus oxychloride (0.1 mole) slowly at $0°$ C. The whole was heated at $100°$ C. for 4 hours. After cooling, the mixture was added to ice water and neutralized with potassium carbonate. Extraction with methylene chloride and removal of the solvent gave 2-chloro-5-methylpyridine in 32% yield.

EXAMPLE 2

Preparation of 2-chloro-5-methylpyridine

To a mixture of acetamide (0.1 mole) and N-propionaldehyde (0.1 mole) in dimethylformamide (50 mL) was added phosphorus oxychloride (0.2 mole) slowly at 0° C. The whole was heated at 100° C. for 4 hours. After cooling, the mixture was added to ice water and neutralized with potassium carbonate. Extraction with methylene chloride and removal of solvent gave 2-chloro-5-methylpyridine in 25% yield.

EXAMPLE 3

Preparation of 2-chloro-5-methylpyridine

To cis-2-pentenonitrile (0.1 mole) in dimethylformamide (50 mL) was added phosphorus oxychloride (0.22 mole) slowly at 0° C. The mixture was heated at 110° C. for 3 hours. After cooling, the mixture was added to ice water an neutralized with potassium carbonate. Extraction with methylene chloride and removal of solvent gave 2-chloro-5-methylpyridine in 40% yield.

While the invention has been illustrated and described in detail in the foregoing description, the same is to be considered as illustrative and not restrictive in character, it being understood that only the preferred embodiment has been described and that all changes and modifications that come within the spirit of the invention are desired to be protected.

What is claimed is:

1. A process for preparing a 2-halo-5-substituted pyridine compound, comprising reacting a dialkylformamide or an arylalkylformamide, in the presence of a halogenating agent, with an amide or nitrile of the formula:

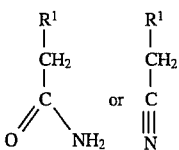

wherein $R^1$ is —H or an alkyl, haloalkyl, alkenyl, aryl, aralkyl, ester or halogen group, and an aldehyde of the formula:

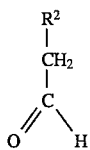

wherein $R^2$ is an alkyl, haloalkyl, alkenyl, aryl, aralkyl, ester or halogen group, so as to form a 2-halo-5-substituted pyridine compound.

2. The process of claim 1 which includes reacting said dialkylformamide or arylalkylformamide with said amide and said aldehyde in the presence of a halogenating agent.

3. The process off claim 1 which comprises reacting said dialkylformamide or arylalkylformamide with said nitrile and said aldehyde in the presence of a halogenating agent.

4. The process of claim 1 wherein said halogenating agent is a chlorinating agent.

5. The process of claim 4 which comprises reacting a dialkylformamide with said amide or nitrile and said aldehyde in the presence of a halogenating agent so as to form a 2-chloro-5-substituted pyridine compound.

6. The process of claim 5 wherein alkyl groups of the dialkylformamide are $C_1$ to $C_{10}$ alkyl groups, $R^1$ is —H or a $C_1$ to $C_{10}$ alkyl group, and $R^2$ is a $C_1$ to $C_{10}$ alkyl or haloalkyl group.

7. The process of claim 6 wherein $R^1$ is —H.

8. The process of claim 7 wherein $R^2$ is an alkyl group.

9. The process of claim 8 wherein the dialkylformamide is dimethylformamide and $R^2$ is a methyl group.

10. A process for preparing a 2-halo-5-substituted pyridine compound, comprising reacting a dialkylformamide or an arylalkylformamide, in the presence of a halogenating agent, with a nitrile of the formula:

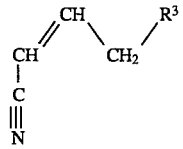

wherein $R^3$ is an alkyl, haloalkyl, alkenyl, aryl, aralkyl or halogen group, so as to form a 2-halo-5-substituted pyridine compound.

11. The process of claim 10 which includes reacting said dialkylformamide with said nitrile in the presence of a halogenating agent so as to form the 2-halo-5-substituted pyridine compound.

12. The process of claim 11 wherein $R^3$ is an alkyl or haloalkyl group.

13. The process of claim 12 wherein said halogenating agent is a chlorinating agent.

14. The process of claim 13 wherein $R^3$ is a $C_1$ to $C_{10}$ alkyl group.

15. The process of claim 14 wherein $R^3$ is a methyl group.

16. The process of claim 15 wherein said chlorinating agent is selected from the group consisting of phosphorus oxychloride, phosophorus pentachloride, phosgene, oxaloyl chloride and thionyl chloride.

17. The process of claim 16 wherein the chlorinating agent is phosphorus oxychloride.

18. A process for preparing 2-chloro-5-methylpyridine, comprising reacting dimethylformamide, in the presence of a chlorinating agent, with (i) either acetonitrile or acetamide together with n-propionaldehyde or (ii) cis-2-pentenonitrile, so as to form 2-chloro-5-methylpyridine.

19. The process of claim 18 which comprises reacting dimethylformamide, in the presence of a chlorinating agent, with acetonitrile and n-propionaldehyde so as to form 2-chloro-5-methylpyridine.

20. The process of claim 18 which comprises reacting dimethylformamide, in the presence of chlorinating agent, with acetamide and n-propionaldehyde so as to form 2-chloro-5-methylpyridine.

21. The process of claim 18 which comprises reacting dimethylformamide, in the presence of a chlorinating agent, with cis-2-pentenonitrile so as to form 2-chloro-5-methylpyridine.

22. The process of claim 18 which is conducted at a temperature of about 20° C. to about 100° C.

23. The process of claim 18 which is conducted under anhydrous conditions.

24. The process of claim 19 which is conducted under anhydrous conditions.

25. The process of claim 20 which is conducted under anhydrous conditions.

26. The process of claim 21 which is conducted under anhydrous conditions.

* * * * *

UNITED STATES PATENT AND TRADEMARK OFFICE
CERTIFICATE OF CORRECTION

PATENT NO. : 5,508,410
DATED : April 16, 1996
INVENTOR(S) : Ramiah Murugan et al.

It is certified that error appears in the above-indentified patent and that said Letters Patent is hereby corrected as shown below:

In col. 4, line 50, please delete "tile" and insert in lieu thereof --the--.

In col. 5, line 59, please delete "off" and insert in lieu thereof --of--.

Signed and Sealed this

Tenth Day of February, 1998

Attest:

BRUCE LEHMAN

*Attesting Officer*  *Commissioner of Patents and Trademarks*